(12) United States Patent
Contreras et al.

(10) Patent No.: US 9,028,844 B2
(45) Date of Patent: May 12, 2015

(54) VACCINE AGAINST TRYPANOSOMA CRUZI INFECTION

(75) Inventors: Roland Contreras, Merelbeke (BE); Kristof De Vusser, Eeklo (BE); Silvia Revelli, Rosario (AR)

(73) Assignees: VIB VZW, Ghent (BE); Universiteit Gent, Ghent (BE)

( * ) Notice: Subject to any disclaimer, the term of this patent is extended or adjusted under 35 U.S.C. 154(b) by 1716 days.

(21) Appl. No.: 12/225,396

(22) PCT Filed: Mar. 14, 2007

(86) PCT No.: PCT/EP2007/052399
§ 371 (c)(1),
(2), (4) Date: Oct. 20, 2010

(87) PCT Pub. No.: WO2007/107488
PCT Pub. Date: Sep. 27, 2007

(65) Prior Publication Data
US 2011/0038887 A1 Feb. 17, 2011

(30) Foreign Application Priority Data
Mar. 17, 2006 (EP) .................................. 06111294

(51) Int. Cl.
A61K 39/005 (2006.01)
A61K 38/16 (2006.01)
C12N 9/00 (2006.01)
C07K 14/44 (2006.01)

(52) U.S. Cl.
CPC .............. *A61K 39/005* (2013.01); *A61K 38/16* (2013.01); *C07K 14/44* (2013.01)

(58) Field of Classification Search
None
See application file for complete search history.

(56) References Cited

U.S. PATENT DOCUMENTS

| 4,298,596 | A | 11/1981 | Snary | |
|---|---|---|---|---|
| 6,248,329 | B1 * | 6/2001 | Chandrashekar et al. | 424/191.1 |
| 7,060,676 | B2 * | 6/2006 | Chuenkova et al. | 514/8.4 |
| 7,491,510 | B2 | 2/2009 | Contreras et al. | |
| 7,993,822 | B2 | 8/2011 | Chen et al. | |
| 2004/0185146 | A1 | 9/2004 | Pelletier | |
| 2005/0158347 | A1 | 7/2005 | Tarleton et al. | |
| 2009/0087882 | A1 | 4/2009 | Contreras et al. | |

FOREIGN PATENT DOCUMENTS

| EP | 0 003 529 | | 8/1979 |
|---|---|---|---|
| GB | 2 000 968 | A | 1/1979 |
| WO | WO 9316199 | | 8/1993 |
| WO | WO 93/18787 | | 9/1993 |
| WO | WO 2007/107488 | A2 | 9/2007 |

OTHER PUBLICATIONS

Todeschini et al The Journal of Biological Chemistry vol. 29 No. 7 Issue of Feb. 13, pp. 5323-5328, 2004.*
Buscaglia et al. 1998 (The repetitive domain of *Trypanosoma cruzi* trans-sialidase enhances the immune response against the catalytic domain; Journal of Infectious Diseases 177(2):431-436).*
Hoft et al. 2003 (Vaccination with the *T. cruzi* trans-sialidase induces both mucosal and systemic protective immunity; AAI 2003: Meeting Abstract).*
Garcia et al., Identification of HLA-A*0201-restricted cytotoxic T-cell epitopes of *Trypanosoma cruzi* TcP2beta protein in HLA-transgenic mice and patients, Microbes and Infection, Apr. 2003, pp. 351-359, vol. 5, No. 5.
Ara et al., CD8+-T-cell-dependent control of *Trypanosoma cruzi* infection in a highly susceptible mouse strain after immunization with recombinant proteins based on amastigote surface protein 2, Infection and Immunity, Sep. 2005, pp. 6017-6025, vol. 73, No. 9.
Gao et al., The *Trypanosome cruzi* trans-sialidase is a T cell-independent B cell mitogen and an inducer of non-specific Ig secretion, International Immunology, Mar. 2002, pp. 299-308, vol. 14, No. 3.
Pitcovsky et al., A functional network of intramolecular cross-reacting epitopes delays the elicitation of neutralizing antibodies to *Trypanosoma cruzi* trans-sialidase, The Journal of Infectious Diseases, Aug. 1, 2002, pp. 397-404, vol. 186, No. 3.
Wizel et al., Human infection with *Trypanosoma cruzi* induces parasite antigen-specific cytotoxic T lymphocyte responses, Journal of Clinical Investigation, Sep. 1, 1998, pp. 1062-1071, vol. 102, No. 5.
Low et al., Amastigote surface proteins of *Trypanosoma cruizi* are targets for CD8+ CTL, Journal of Immunology, Feb. 15, 1998, pp. 1817-1823, vol. 160, No. 4.
Woronowicz et al., Trypanosome trans-sialidase targets TrkA tyrosine kinase receptor and induces receptor internalization and activation, Glycobiology, Nov. 2004, pp. 987-998, vol. 14, No. 11.
Wizel et al., Identification of *Trypanosoma cruzi* trans-sialidase family members as targets of protective CD8+ TC1 responses, Journal of Immunology, Dec. 15, 1997, pp. 6120-6130, vol. 159, No. 12.
Pitcovsky et al., Epitope mapping of trans-sialidase from *Trypanosoma cruzi* reveals the presence of several cross-reactive determinants, Infection and Immunity, Mar. 2001, pp. 1869-1875, vol. 69, No. 3.
Fujimura et al., DNA sequences encoding CD4+ and CD8+ T-cell epitopes are important for efficient protective immunity induced by DNA vaccination with a *Trypanosoma cruzi* gene, Infection and Immunity, Sep. 2001, pp. 5477-5486, vol. 69, No. 9.
PCT International Search Report, PCT/EP2007/052399 dated Nov. 15, 2007.
Araujo et al., CD8+-T-cell-dependent control of *Trypanosoma cruzi* infection in a highly susceptible mouse strain after immunization with recombinant proteins based on amastigote surface protein 2, Infection and Immunity, Sep. 2005, pp. 6017-6025, vol. 73, No. 9.
Chuenkova et al., trans-Sialidase of *Trypanosoma cruzi*: Location of Glactose-Binding Site(s), Biochemical and Biophysical Research Communication, 1999, pp. 549-556, vol. 262.

* cited by examiner

*Primary Examiner* — Ja'Na Hines
*Assistant Examiner* — Mary Lyons
(74) *Attorney, Agent, or Firm* — TraskBritt, P.C.

(57) ABSTRACT

The present invention relates to a vaccine against *Trypanosoma cruzi* infection, useful in the prevention and/or treatment of the Chagas disease. More specifically, the present invention relates to a recombinant mutant trans-sialidase enzyme that can be used as an efficient vaccine, without side effects.

5 Claims, 8 Drawing Sheets

Figure 12

VACCINE AGAINST *TRYPANOSOMA CRUZI* INFECTION

CROSS-REFERENCE TO RELATED APPLICATIONS

This application is a national phase entry under 35 U.S.C. §371 of International Patent Application PCT/EP2007/052399, filed Mar. 14, 2007, designating the United States of America and published in English as International Patent Publication WO 2007/107488 A2 on Sep. 27, 2007, which claims the benefit under Article 8 of the Patent Cooperation Treaty to European Patent Application Serial No. 06111294.2, filed Mar. 17, 2006.

TECHNICAL FIELD

The instant disclosure relates to a novel vaccine against *Trypanosoma cruzi* infection, useful in the prevention and/or treatment of the Chagas disease. More specifically, the disclosure relates to a recombinant mutant trans-sialidase enzyme that can be used as an efficient vaccine, without side effects, whereby the vaccine is protecting both against the parasitemia and against the tissue damage caused by the parasites.

BACKGROUND

One of the most common diseases in both South America and Central America is Chagas disease or American Trypanosomiasis. This disease is caused by the flagellated parasite *Trypanosoma cruzi* and is spread by the blood-sucking insect *Triatoma infestans*. Once the parasite gets into the wound created by the insect bite, it spreads throughout the body and invades host cells. Inside a host cell, the parasite transforms into a non-infective amastigote, which is able to multiply very fast. When the amount of parasites inside the cell numbers about 500, the parasites transform back into the infective trypomastigote stage. Shortly after, the cell bursts, setting the parasites free in the blood from where they can infect new cells. The disease has three phases. The first phase is the acute phase, which occurs just after infection and has only mild symptoms. The second phase is the latent phase, which can have a duration of three to ten years and is asymptomatic. The third phase is the chronic phase, during which all infected tissues are deteriorating due to large-scale cell lysis, which eventually leads to the death of the patient. Seventy percent of Chagasic patients die from a heart attack caused by severe heart damage.

The molecular mechanism by which the parasite infects the host cells is very complex and has been the topic of a lot of research projects throughout the years. This research has shown that *T. cruzi* expresses a unique sialic acid-transferring enzyme, which is able to cleave off $\alpha$-2,3 bound sialic acids and transfer them to terminal $\beta$-1,4 galactose residues: the trans-sialidase (TS). The enzyme is anchored in the parasite cell membrane by a GPI anchor, but it is also shed in the blood after cleavage by a parasite lipase enzyme. The trans-sialidase plays an essential role in the infection cycle of *T. cruzi* since it makes the invasion of host cells possible. Experiments have shown that when trans-sialidase activity is inhibited (for example, by using mutant cell lines that do not have sialic acid on their surface (Ciavaglia et al., 1993; Ming et al., 1993; and Schenkman et al., 1993) or by blocking the acceptor molecules on the parasite surface (Yoshida et al., 1989; Schenkman et al., 1991; and Ruiz et al., 1993) the invasion of the host cells by the parasite is inhibited. Additionally, the trans-sialidase also plays a role in the parasite's defense mechanism against the host immune system because it is used to cover the surface of the parasite with sialic acid molecules, which make it very difficult for the immune system of the host to detect the parasite.

Because the trans-sialidase enzyme is of such an important role in infection cycle and defense, the parasite developed several methods to protect the enzyme against the host immune system. First, the parasite expresses more than 200 different trans-sialidases, of which only about 15 are active (El-sayed et al., 2005). This makes it very hard for the immune system to inhibit invasion of host cells by the parasite in a normal infection cycle, especially because the parasites and their trans-sialidases reside only a short time in the bloodstream before they enter a host cell, where they are protected from the immune system. Moreover, the trans-sialidases have a very long immunodominant tail of SAPA repeats, which act as a diversion for the immune system, successfully luring away antibodies from the important catalytic site of the enzyme.

Currently, there are two drugs used to counter the disease: Benznidazole and Nifurtimox. There is very little known about their mechanism, but it is known that they induce oxidative stress in cells. Both products do not differentiate between parasites and host cells, resulting in severe side-effects for the patient. Because of these side-effects and because they have a very limited efficiency in chronic patients, these drugs have only a limited use.

Vaccination could solve these problems. A vaccine would probably be a lot more effective in treating chronic patients than the existing medication and it would have the advantage of having a preventive effect as well. GB2000968 discloses a vaccine based on killed trypanosome. However, trypomastigotes are difficult to culture in high density, and the immunogenic capacity of the vaccine is low. Several other patent applications have described a microsomal fraction (EP0003529), a glycoprotein fraction (U.S. Pat. No. 4,298,596) or a peptide (WO9316199) derived from *T. cruzi* as a possible vaccine. However, none of these vaccines proved to be sufficiently efficient.

Because of its essential role in the infection and due to the fact that the enzyme is both well exposed on the cell surface and present as a free molecule in the blood and, therefore, a good target for antibodies, the trans-sialidase may be a good antigen candidate for the production of a vaccine against Chagas disease. A vaccine based on the trans-sialidase enzyme is not expected to have important side-effects because there are no homologues of the trans-sialidase in humans, which means that all generated antibodies would be parasite-specific. Several authors have disclosed vaccination based on delivery of DNA encoding trans-sialidase (Costa et al., 1998; Vasconcelos et al., 2004), possibly in combination with IL-12 (Katae et al., 2002). In the study of trans-sialidase DNA vaccination of Pereira-chioccola et al. (1999), recombinant trans-sialidase was used as control. This recombinant trans-sialidase was shown to elicit trans-sialidase-inactivating antibodies and could lower the trypomastigote-induced parasitemia in mice. However, the trans-sialidase is inefficient as antigen due to the immunodominant tail. Therefore, the use of the wild-type active parasite enzyme in vaccination is not suitable, as the high doses of recombinant trans-sialidase needed could induce side-effects, especially because it was shown that active trans-sialidase is able to activate neuronal receptors (Woronowicz et al., 2004). US2005158347 discloses a multi-component vaccine against *T. cruzi* comprising trans-sialidase or a polynucleotide encoding trans-sialidase. However, the drawbacks related to the use of trans-sialidase, as cited above, are also valid for this multi-component vaccine.

DISCLOSURE

Surprisingly, it was found that mutants with limited or no enzymatic activity can be successfully used as vaccine. This is unexpected, as one would not expect that antibodies against these inactive mutants are still able to inactivate the enzymatic activity of wild-type trans-sialidase and/or to inhibit the infection cycle. Even more surprisingly, we were able to make the vaccine more efficient by engineering the trans-sialidase (TS) in such a way that the immunodominant tail of SAPA repeats is no longer present. The engineered mutant trans-sialidase enzyme can be used as an efficient vaccine against Chagas disease in mice. Most surprisingly, the mutant trans-sialidase (Mut TS) form protects the immunized animals against tissue damage in heart and skeletal muscle (myocarditis and myositis) and against splenomegaly, while animals immunized with wild-type trans-sialidase are still affected.

Disclosed is the use of an enzymatically inactive *Trypanosoma* trans-sialidase mutant protein as a medicine. "Enzymatically inactive trans-sialidase mutant protein," as used herein, means that the remaining sialidase activity and/or transferase activity is less than 20% of the wild-type activity, preferably less than 10% of the wild-type activity, even more preferably less than 5% of the wild-type activity. Sialidase and transferase activity are quantitated separately, as described in the materials and methods to the examples. Preferably, the *Trypanosoma* is *T. cruzi*. Preferably, the mutant trans-sialidase is a recombinant trans-sialidase. Preferably, the mutant trans-sialidase lacks the immunodominant SAPA repeats tail. Even more preferably, the mutant trans-sialidase comprises SEQ ID NO:1; most preferably, the mutant trans-sialidase consists of SEQ ID NO:1. A preferred embodiment is an enzymatically inactive mutant according to the invention, of which the glycosylation profile is different from the glycosylation profile in the wild-type trypanosomes. As a non-limiting example, such different glycosylation profile can be obtained by production of the mutant enzyme as a recombinant mutant enzyme in a non-mammalian host cell, preferably a yeast cell, even more preferably a *Pichia* yeast, most preferably *Pichia pastoris* GS115 or any engineered *Pichia pastoris* strain that is derived from the GS 115 strain. Preferably, the enzymatically inactive mutant shows an N-glycan profile that predominantly exists of M8GlcNAc2. "Predominantly," as used herein, means that the most important peak in the N-glycan analysis consists of the M8GlcNAc2 fraction.

Also disclosed is the use of an enzymatically inactive *Trypanosoma* trans-sialidase mutant protein for the preparation of a vaccine. Optionally, the enzymatically inactive *Trypanosoma* trans-sialidase may by mixed with other suitable antigens. Optionally, adjuvants and/or cytokines may be added to the vaccine to improve the immune response. As a non-limiting example, a suitable adjuvant has been described in WO0160404, suitable cytokines are, as non-limiting examples, Interleukin-6 and Interleukin-12. Preferably, *Trypanosoma* is *Trypanosoma cruzi* and the vaccine is used in the prophylactic and/or therapeutic treatment of Chagas disease. Preferably, the mutant trans-sialidase is a recombinant trans-sialidase. Preferably, the mutant trans-sialidase lacks the immunodominant SAPA repeats tail. Even more preferably, the mutant trans-sialidase comprises SEQ ID NO:1; most preferably, the mutant trans-sialidase consists of SEQ ID NO:1. A preferred embodiment is an enzymatically inactive mutant hereof, of which the glycosylation profile is different from the glycosylation profile in the wild-type trypanosomes.

Further disclosed is a pharmaceutical composition comprising an enzymatically inactive *Trypanosoma* trans-sialidase mutant protein as a vaccine. Preferably, *Trypanosoma* is *Trypanosoma cruzi* and the vaccine is used in the prophylactic and/or therapeutic treatment of Chagas disease. Preferably, the mutant trans-sialidase is a recombinant trans-sialidase. Preferably, the mutant trans-sialidase lacks the immunodominant SAPA repeats tail. Even more preferably, the mutant trans-sialidase comprises SEQ ID NO:1; most preferably, the mutant trans-sialidase consists of SEQ ID NO:1. A preferred embodiment is an enzymatically inactive mutant according to the invention, of which the glycosylation profile is different from the glycosylation profile in the wild-type trypanosomes.

Also disclosed is the use of an enzymatically inactive *Trypanosoma* trans-sialidase mutant protein as described herein, to protect mammals (including humans) from myocarditis and/or myositis and/or splenomegaly caused by *Trypanosoma cruzi* infection.

Preferably, the mutant trans-sialidase lacks the immunodominant SAPA repeats tail. Even more preferably, the mutant trans-sialidase comprises SEQ ID NO:1; most preferably, the mutant trans-sialidase consists of SEQ ID NO:1. A preferred embodiment is an enzymatically inactive mutant hereof, of which the glycosylation profile is different from the glycosylation profile in the wild-type trypanosomes.

BRIEF DESCRIPTION OF THE DRAWINGS

FIG. 4: Sialidase activity of the trans-sialidase mutant. The sialidase activity of the trans-sialidase mutant that was used in this project was determined by measuring the amount of free methylumbelliferone in the reaction mix after reaction of the enzyme with the 4-methylumbelliferyl-N-acetylneuraminic acid substrate. Measurement of the amount of fluorescence was done with a CYTOFLUOR® Multi-Well Plate Reader Series 4000 (PerSeptive Biosystems).

Log rank test (Test Statistics for Equality of Survival Distributions):
Differences between all groups: $p<0.00001$
Differences between G1-G2-G6: $p=0.8404$
Differences between G3-G4-G5-G7: $p=0.5201$

Kruskal Wallis Test:
Day 14 pi
Differences between all groups: $p<0.0001$
Differences between G1-G2-G6: $p=0.553$
Differences between G3-G4-G5-G7: $p=0.224$
Day 21 pi
Differences between all groups: $p<0.0001$
Differences between G1-G2-G6: $p=0.266$
Differences between G3-G4-G5-G7: $p=0.073$

FIG. 9: Representative results of histopathological analysis in immunized and non-immunized mice. BALB/c mice were injected with 100 bloodstream forms and organs were collected 60 days pi. Paraffin-embedded sections were stained with hematoxylin and eosin, and examined with a light microscope at the following magnifications: ×200 and ×400 (Panels B, C, E. F, H, I) ×400 (Panel G) or ×400 and ×600 (Panels A, D). See text for details of preparation and description of morphology.

DETAILED DESCRIPTION

Examples

Materials and Methods to the Examples

Random Mutagenesis of the Trans-Sialidase Gene

The trans-sialidase gene, which was cloned in our lab and which lacks the part coding for the immunodominant repeats (Laroy et al.,) 2000), was mutated by using a PCR-based mutagenesis technique on the pPICZTSjE plasmid. In this method, random mutations are created in the gene by the error-prone Taq DNA polymerase. The frequency of errors is increased by using unequal concentrations of dNTPs (0.2 mM dATP and dGTP/1 mM dCTP and dTTP) and by adding 0.1 mM $Mn^{2+}$ to the reaction mixture.

Transformation to *Pichia pastoris*

The mutated PCR fragments were ligated into the original pPICZTSjE vector and the plasmids were transformed to the methylotrophic yeast *Pichia pastoris*. Prior to transformation, the plasmids were linearized by a SacI restriction digest to make insertion into the yeast genome easier. Transformation of the plasmid DNA to *Pichia pastoris* GS115(his4) was done by electroporation according to the manufacturer's instructions (Invitrogen). Selection was done on YPDS plates containing the antibiotic ZEOCIN™ (100 µg/ml). With a Flexys colony picker robot (Genomic) Solutions), all transformants were put in individual wells of 96-well plates that were prefilled with YPD medium. Cells were grown for 24 hours at 30° C. and were then stamped on solid YPD plates for stockage and future analysis.

Screening of Transformants for Inactive Trans-Sialidase-Expressing Clones

Transformants were grown in 150 μl BMGY medium in 96-well plates. After 24 hours, trans-sialidase expression was induced by changing the BMGY medium to minimal medium (100 mM phosphate buffer pH 7+1.34% YNB+1% CSM+1% methanol). Expression was allowed for 28 hours and 1% methanol was added every 12 hours. Five μl of induction medium of each transformant was used for the enzymatic assay. To analyze the enzymatic activity of the expressed trans-sialidases, a fluorescence assay was used. The reaction mixture that was put in each well of a 96-well plate consisted of 20 μM lactose-AMAC, 0.4 mM sialyllactose, 20 mM Hepes pH 7.2 and 10% induction medium (total reaction volume is 50 μl). After 1 hour incubation at 37° C., the reaction is stopped by adding 150 μl $H_2O$. Collection of sialylated molecules is done with anion exchanger resin (QAE-sephadex, SIGMA) in a 96-well filtration plate (Millipore). Before adding the samples, the resin is prewetted with 200 μl $H_2O$ and the liquid is removed by centrifugation at 1000 rpm. After four washes with 200 μl $H_2O$, the sialylated molecules are eluted into a 96-well clear bottom plate with 150 μl 1 M ammoniumacetate. Fluorescence is measured with the LUMI-IMAGER™ (Boehringer) at 520 nm. To separate true inactive trans-sialidase-expressing clones from clones expressing only a part of the trans-sialidase (due to a stop codon that was created by the mutagenesis), the data from the fluorescence assay were combined with data from an ELISA, which was done according to standard protocols. For the ELISA, 5 μl of induction medium of each transformant was used and the trans-sialidase was detected with anti-E-tag antibody followed by a peroxidase-coupled secondary antibody. Chemiluminescence was measured with the LUMI-IMAGER™ (Boehringer).

Purification of Trans-Sialidase

For purification, the *Pichia pastoris* strain, which expresses the trans-sialidase, was grown in 600 ml BMGY. At $A_{600}$ of 15, induction was started in 600 ml BMMY. Expression was allowed for 28 hours and 1% methanol was added every 12 hours. Expression medium was collected and filtered (0.45 µm filter, Millipore). To avoid protein degradation, protease inhibitors were added (one tablet of Complete Protease Inhibitor Cocktail, Roche). The culture medium was applied to a 5 ml pre-packed anti-E-tag column (Pharmacia Biotech) equilibrated with binding buffer (0.2 M phosphate, 0.05% $NaN_3$, pH 7) at a flow rate of 2 ml/minute using an FPLC system (Pharmacia Biotech). After this, the column was washed extensively with binding buffer. The trans-sialidase was eluted with 1 M glycine pH 3. Fractions of 2.7 ml were collected in tubes containing 0.3 ml neutralization buffer (1 M Tris-HCl pH 8.8). Fractions were analyzed for the presence of trans-sialidase by SDS-PAGE. Protein concentration was determined with the method of Bradford (M. M. Bradford, 1976). The average yield of the trans-sialidase was about 1 mg/liter expression medium.

Detailed Analysis of the Enzymatic Activity of the Mutant Trans-Sialidase

The mutant trans-sialidase that was selected for use in this project was analyzed in more detail: both the sialidase activity and the transferase activity were quantitated.

The transferase activity was measured in 20 mM Hepes pH 7.2, 20 µM N-acetylneuraminyl lactose and 220 nM APTS-labeled NA2FB sugar structures (asialo-, galactosylated biantennary, core-substituted with fucose and with bisecting GlcNAc) in a total reaction volume of 50 µl. The NA2FB sugar structures were labeled and purified according to the protocol as was described previously (Callewaert et al., 2001). Fifty ng of purified enzyme was added and the reaction was incubated at 25° C. for 30 minutes. The reaction was stopped by adding 150 µl of water and placing the tubes at −20° C. The reaction mixture was then dried by vacuum evaporation and reconstituted in 5 µl of water. For the analysis of the glycan structures, we used the DSA-FACE technology as was described previously (Callewaert et al., 2001). The sialidase activity of the enzyme was measured in 20 mM Tris-HCl pH 7.6, 30 mM NaCl and 0.2 mM 4-methylumbelliferyl-N-acetylneuraminic acid (MUNANA) in a final volume of 50 pi at a temperature of 25° C. For the assay, 1 µg of purified trans-sialidase was used. After 15 minutes incubation, the reaction is stopped by adding 150 µl 0.2 M carbonate and the fluorescence of free 4-methylumbelliferone is measured with a CYTOFLUOR® Multi-Well Plate Reader Series 4000 (PerSeptive Biosystems).

Mice and Parasites

Adult male BALB/c mice (13 to 14 weeks of age) from the animal facilities of the Veterinary School of La Plata (National University of La Plata) were used. During the experiment, mice were kept in the animal facilities at the School of Medicine of Rosario. Animals had access to food and water ad libitum and they were kept under constant temperature conditions (22-24° C.), establishing a 12 hours light period. Trypomastigotes of the Tulahuén strain of *Trypanosoma cruzi* (Tc) were obtained from the blood of infected mice. The heparinized sample was diluted in physiological solution (PS) and the parasites were counted using a Neubauer's chamber.

Immunizations

Three immunizations (separated by 14 days) have been made with each protein. For the first immunization, Complete Freund Adjuvant (Adj) was used; for the following immunizations, Incomplete Freund Adjuvant (Adj) was used) (SIGMA).

OCH1, 30 µg by subcutaneous route. Vf 0.1 ml/mouse: 50% TS+vehicle (buffer=75% glycine 1 M ph=3+25% phosphate 0.2 M pH=7), +50% Adj.

WT, 30 µg by subcutaneous route; for the rest idem.

Mut, 30 µg by subcutaneous route; for the rest idem.

Alb, ovalbumine (SIGMA) was used as irrelevant protein for the control groups (indicated as OVA).

Experimental Design
  G1 vehicle+Tc (n=10)
  G2 Adj+vehicle+Tc (n=10)
  G3 Adj+WT+Tc (n=10)
  G4 Adj+OCH1+Tc (n=10)
  G5 Adj+Mut+Tc (n=10)
  G6 Adj+Alb+vehicle+Tc (n=10)
  G7 Adj+OCH1 (two doses)+Tc (n=10)
  G8 vehicle+PS (n=5)
  G9 Adj+vehicle+PS (n=5)
  G10 Adj+WT+PS (n=5)
  G11 Adj+OCH1+PS (n=5)
  G12 Adj+Mut+PS (n=5)
  G13 Adj+Alb+vehicle+PS (n=5)
  G14 Adj+OCH1 (two doses)+PS (n=5)

Challenge with *Trypanosoma cruzi*

Fourteen days after the last immunization, the mice were challenged with 100 trypomastigotes per mouse by subcutaneous route. Groups 8-14 received PS.

The acute infection in vivo was monitored by evaluating survival, animal weight and parasitemia.

Histopathological Study

Organs (heart, thymus, spleen, striated muscle and liver) were collected and weighed at 60 days post-infection, washed in PBS, and fixed in 10% buffered formalin for 24 hours. Contiguous 5 µm sections were mounted and stained with hematosylin-eosine and Masson's trichrome following standard procedures.

Tissue parasitism and inflammation were evaluated according to extent of inflammation as previously described by Roggero et al. (2002).

Example 1

Random Mutagenesis of the Trans-Sialidase Gene

Figure 1:
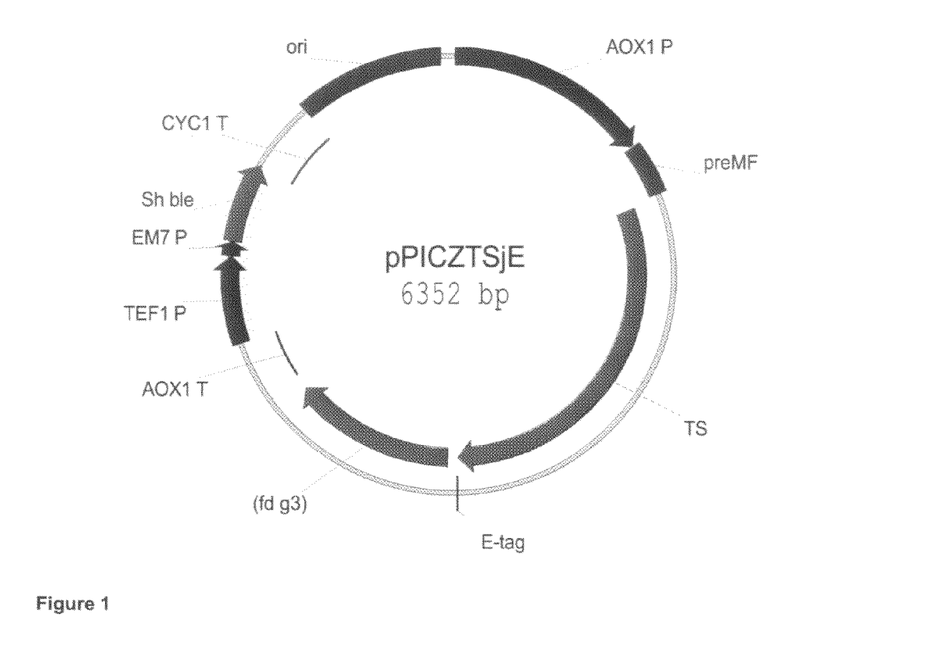
FIG. 1: The pPICZTSjE plasmid containing the trans-sialidase gene. AOX1 P=methanol inducible promoter AOX1, preMF=yeast mating factor (secretion signal), TS=trans-sialidase gene, E-tag=affinity tag, (fd g3)=bacterial DNA with no function, AOX1 T=AOX1 terminator sequence, TEF1 P=yeast promoter, EM7 P=bacterial promoter, Sh ble=ZEOCIN™-resistance marker, CYC1 T=Cytochrome C terminator sequence, ori=origin of replication.

By using a PCR-based mutagenesis technique on the pPIC-ZTSjE plasmid) (FIG. 1), we were able to create mutations in the trans-sialidase gene. The method is based on the use of the error-prone Taq DNA polymerase. By using high amounts of this enzyme in the reaction and by adding unequal amounts of dNTPs and $Mn^{2+}$ to the PCR mix, the frequency of these errors was increased. The technique was optimized to make sure that, on average, there was only one mutation per PCR product. The mutated trans-sialidase gene was ligated into the original pPICZTSjE vector where it replaced the original gene.

Figure 2:
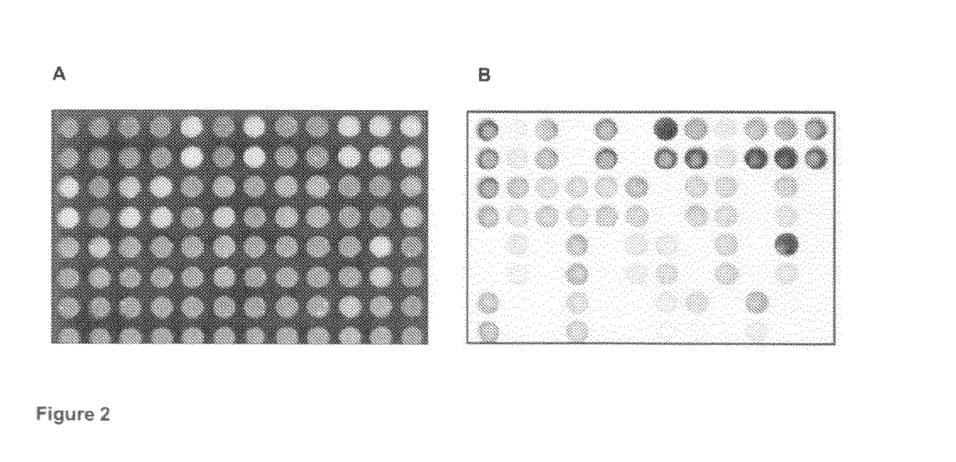
FIG. 2: Combination of fluorescence assay data with ELISA data as screening method. A=96-well clear bottom plate visualized with the LUMI-IMAGER™. The fluorescence is a measure for the amount of trans-sialidase activity in the induction medium of each transformant. B=ELISA in 96-well protein binding plate. The full-size trans-sialidase in the induction medium of each transformant was detected with an anti-E-tag antibody directed against the C-terminal E-tag.)

The plasmids carrying the mutated trans-sialidase gene were transformed to the methylotrophic yeast *Pichia pastoris* and transformants were put in 96-well plates by a Flexys colony picker robot (Genomic Solutions). The collection of transformants was then screened for clones expressing an inactive trans-sialidase with a fluorescence assay, which used a fluorescently labeled acceptor molecule (lactose-AMAC) and a high amount of sialic acid donor molecules (sialyllactose). After the reaction with the trans-sialidase in the induction medium of the transformants, the sialylated molecules were collected with anion exchanger resin in a 96-well filtration plate and eluted into a clear bottom 96-well plate. The amount of sialyllactose-AMAC could then be measured with a LUMI-IMAGER™ (Boehringer) and was a measure for the activity of the trans-sialidase expressed by the different transformants. To exclude transformants who only expressed a partial trans-sialidase due to the insertion of an early stop codon by the mutagenesis, the data from the fluorescence assay were combined with the data from an ELISA, in which we used an antibody against the C-terminal E-tag (FIG. 2). In this way, several transformants could be identified that expressed a trans-sialidase with very little to no enzymatic activity continuing.

Example 2

Purification of Recombinant Trans-Sialidase

Figure 3:
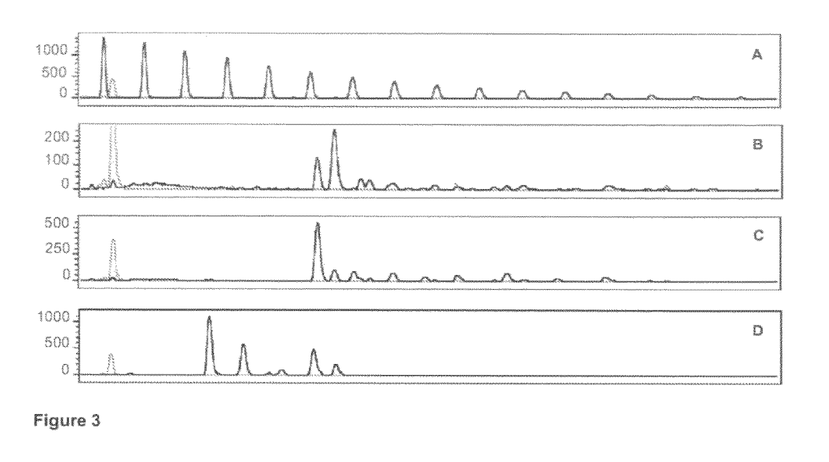
FIG. 3: Glycoprofiles of trans-sialidase that was produced in *Pichia pastoris* GS 115 (WT) and *Pichia pastoris* Glycoswitch M8 (OCH 1). Recombinant trans-sialidase was produced in *Pichia pastoris* GS 115 and in *Pichia pastoris* GS 115 Glycoswitch M8, a strain in which hyperglycosylation has been shut down via the knock-out of the OCH1 activity. N-glycans of the secreted trans-sialidases were analyzed with the DSA-FACE technology. The N-glycans on the trans-sialidase produced in *Pichia pastoris* GS 115 Glycoswitch M8 are predominantly M8GlcNAc2.

Because of the presence of an E-tag at the C-terminal end of the trans-sialidase, the enzyme could be purified to near homogeneity with one single step using affinity chromatography. Three different forms of the trans-sialidase were purified for this project: the active trans-sialidase that was cloned in our lab and was expressed in the *Pichia pastoris* strain GS115(his4) (Laroy et al., 2000) (WT), the same enzyme but expressed in the *Pichia pastoris* GS115(his4) Glycoswitch M8 strain, a yeast strain in which hyperglycosylation has been shut down via the knock-out of the OCH1 activity (Vervecken et al., 2004) (OCH1) (FIG. 3) and a mutant trans-sialidase, which was selected from the collection of mutants we created via random mutagenesis and which was expressed in the *Pichia pastoris* strain GS115(his4) (Mut). All trans-sialidases that were used in this project lacked the immunodominant SAPA repeats tail, which is present on almost all trans-sialidases derived from the parasite itself.

Figure 4:
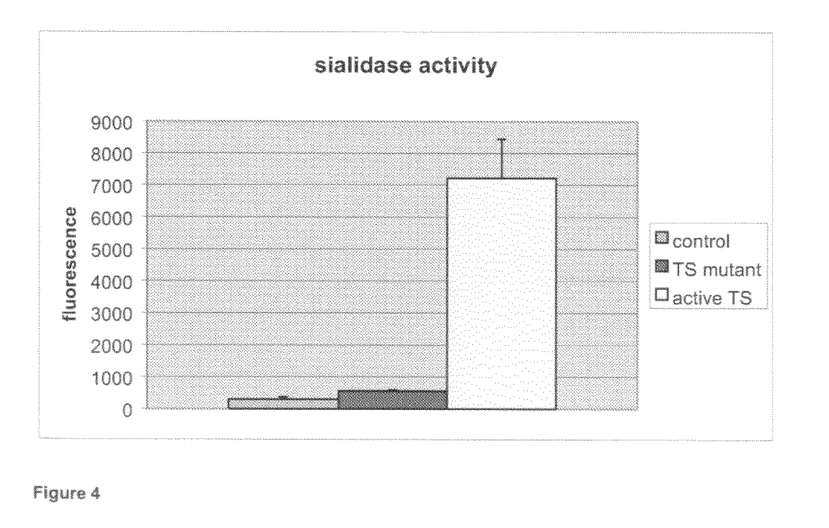
Figure 5:
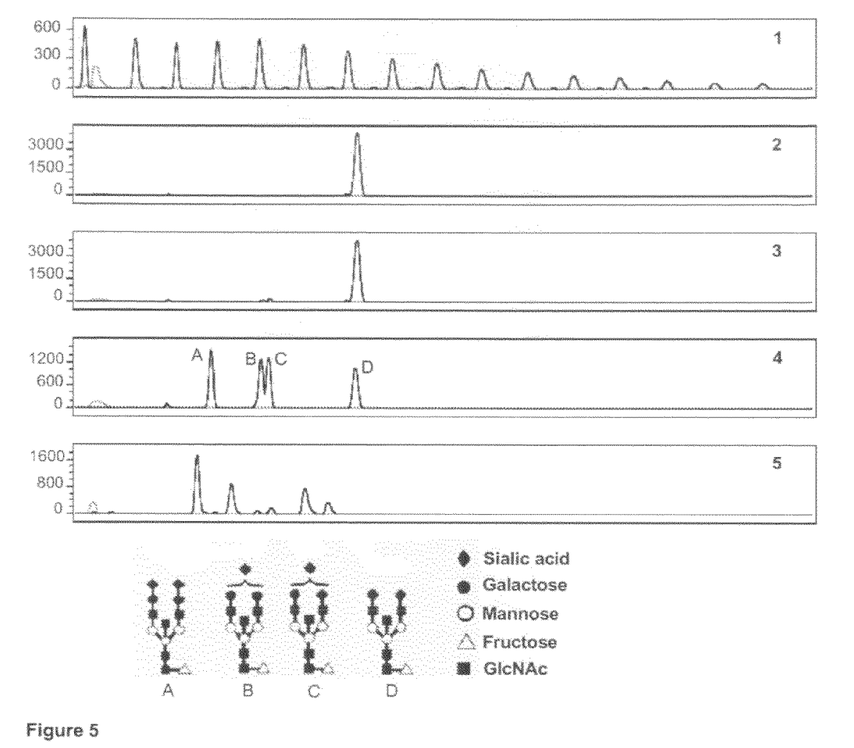
FIG. 5: Transferase activity of the trans-sialidase mutant. 1=dextran ladder, 2=control, 3=mutant TS, 4=active TS, 5=RNase B standard glycan profile. The transferase activity of the mutant trans-sialidase that was used in this project was determined by analyzing the amount of sialylated NA2FB glycans (asialo-, galactosylated biantennary, core-substituted with fucose and with bisecting GlcNAc) with the DSA-FACE technology.

The enzymatic activity of the mutant that was selected to be used in this project has been analyzed in more detail. Both the sialidase activity and the transferase activity were measured with highly sensitive assays. The data showed that the mutant used in this project had only about 3.6% sialidase activity (FIGS. 4) and 4.5% transferase activity continuing (FIG. 5). This mutant was selected because it showed no activity in the fluorescence assay and showed a very good expression in the ELISA.

To further characterize the systemic consequences of TSs immunizations and the possible changes in the kinetic properties of OCH1 protein, an in vivo experiment was carried out. TSs proteins were subcutaneously administered in mice and their concentration was monitored in blood samples taken at different times after injection. Simultaneously, a histopathological analysis was run. Tissue alterations (i.e., thymus atrophy) were not observed during the whole experimental course. No detectable values were recorded in measurements carried out at 1, 3, 4 days after injection. After 15, 20 and 30 days post-inoculum, the three recombinant TS showed similar circulating levels. Kinetic data were further confirmed by Western blots of serum samples employing a monoclonal anti-E-tag antibody.

Collectively, it can be concluded that the recombinant proteins used herein did not induce histopathological alterations per se, in any of the studied organs. It has to be noted, however, that the relevant tissue for wt TS is the nervous system where neurodifferentiating activity could perhaps be found. Furthermore, OCH1 TS recombinant protein, which lacks the hyperglycosylation motif, did not change its concentration and stabilization in blood in respect to WT and MUT.

Example 3

Vaccination Experiments

Figure 6:
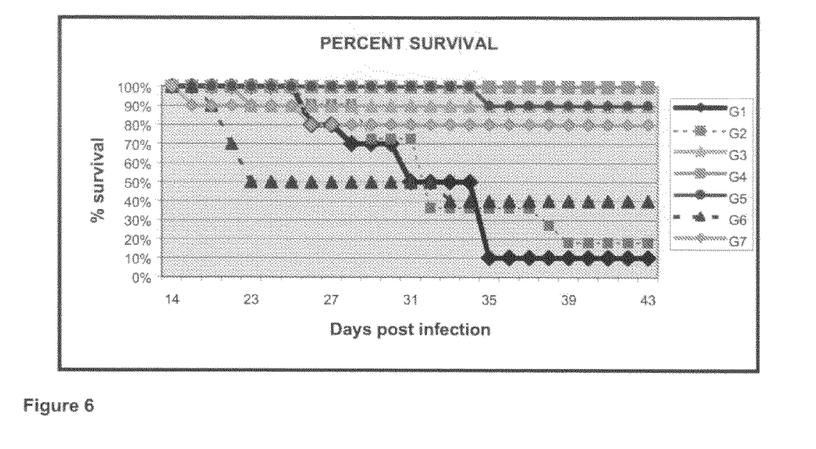
FIG. 6: Mortality of test animals. Graphical presentation of the number of surviving animals at different time points after the infection with *T. cruzi* parasites.
Figure 7:
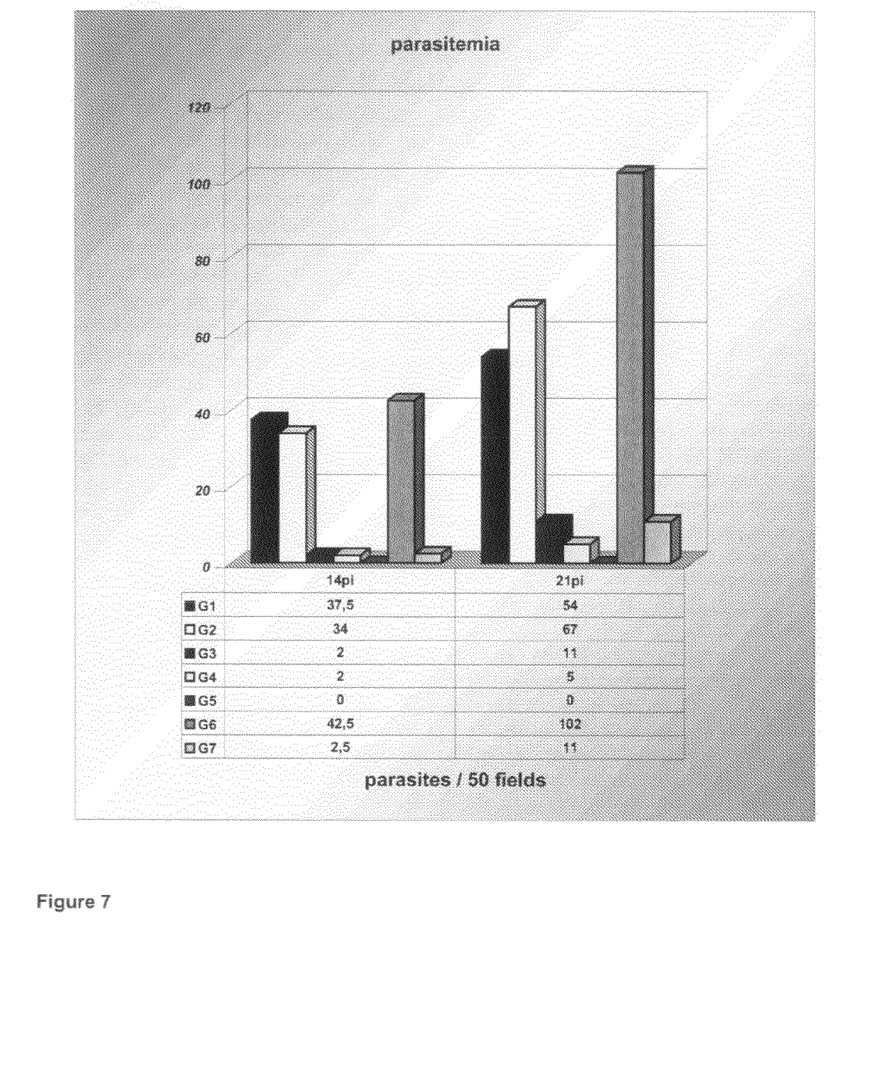
FIG. 7: Parasitemia in test animals The number of parasites in the blood of the mice was checked at 14 and 21 days post-infection. Parasites in 5 µl of blood that was obtained from the tail of the mice were counted with a Neubauer's chamber. The results are expressed as number of parasites/50 microscopic fields (400×).
Figure 8:
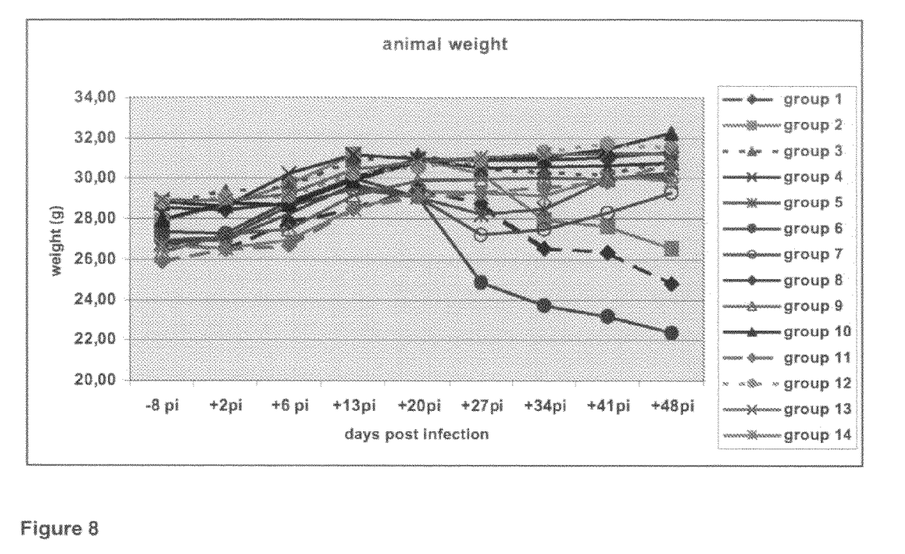
FIG. 8: Weight of test animals. Graphical presentation of the body weight of the animals that was determined on a weekly basis.

Fourteen groups of mice were used for these experiments and each group was given a different treatment. Groups 1-7 were challenged with *Trypanosoma cruzi* parasites 14 days after the last immunization, while groups 8-14 functioned as a control and were given physiological solution (PS) instead. Groups 1-7 consisted of ten mice each, while groups 8-14 consisted of five mice each. The acute infection in the animals was monitored by evaluating survival, animal weight and parasitemia. The survival was checked by a daily mortality control and the animal weight was registered on a weekly basis. The parasitemias were studied by direct microscopic observation in standard conditions. At 14 and 21 days post-infection, 5 µl of blood obtained from the tail of infected mice was analyzed; the results were expressed as number of parasites/50 microscopic fields (400×). The results show that there was 80 to 100% survival in the animals that were vaccinated with trans-sialidase. In contrast, the animals that were not vaccinated with trans-sialidase only showed a survival of 20%. The mutant trans-sialidase was even more efficient than the active trans-sialidase in these experiments (FIG. 6). When the parasitemia were checked in the different groups, it was shown that in non-vaccinated animals, the number of parasites in the blood was high, while in animals that were vaccinated with the trans-sialidase the number of parasites in the blood was very low (FIG. 7). When looking at the number of parasites in the blood, it was shown that the mutant trans-sialidase had a better effect than the active trans-sialidase. Also, the active trans-sialidase that was expressed in a yeast strain in which hyperglycosylation has been shut down showed a better effect than the active trans-sialidase that was expressed in a yeast strain was still able to synthesize hyperglycosylated proteins. This can be explained by the fact that the trans-sialidase that was expressed in the yeast strain with a defective hyperglycosylation will most likely be less rapidly cleared from the mouse body, which involves that it will have a longer lasting effect in the bloodstream of the mouse. An alternative explanation for this could be the fact that the protein part of glycoproteins is far more accessible for antibodies in the strain in which hyperglycosylation has been shut down, due to the smaller glycans on these glycoproteins. When the weight of the animals was checked, it was shown that the animals that were vaccinated with trans-sialidase had a normal weight, while a significant decrease in the weight of the non-vaccinated infected animals was observed (FIG. 8).

Example 4

Figure 9:
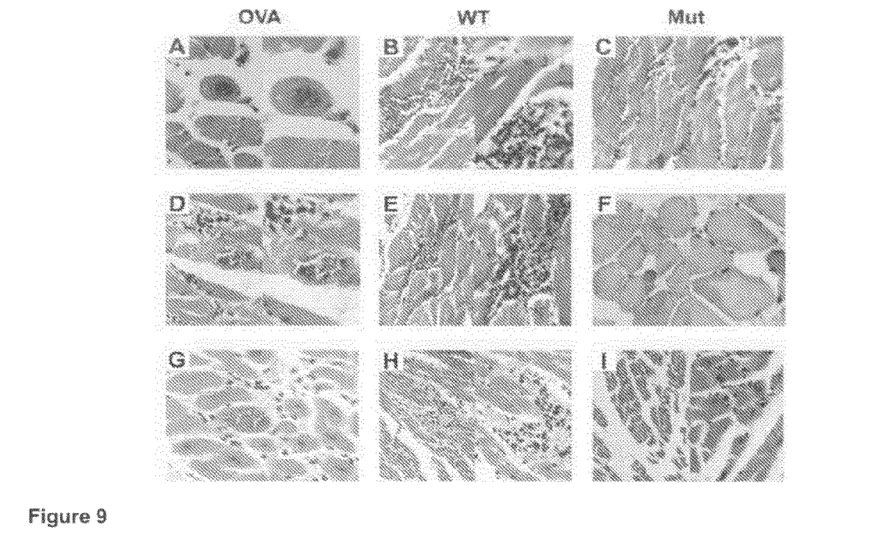

Mut (but not OCH1) Immunization Induces Protection from Tissue Damage in Experimental *T. cruzi* Infection The present results, as well as some published studies, demonstrate that immunization with different proteins of *T. cruzi* (or its gene by genetic immunization) can enhance the survival of mice infected with *T. cruzi*. However, in none of these former studies, the immunizations prevent in high proportion the tissue damage in infected animals. For this analysis, sections from heart, thymus, spleen, striated muscle and liver from mice immunized and challenged with *T. cruzi* were assessed at 60 days post-infection (late stage of infection) for tissue parasite burden and inflammation. Parasite persistence and hence disease severity in this mouse model of *T. cruzi* infection is highest in heart and skeletal muscle, and so these tissues were the primary focus of attention. Irrespective of immunization conditions, all mice groups exhibited no amastigotes nests in skeletal muscles and heart (FIG. 9, Panels B, C, E, F, H, I and Table 1). In comparison, non-immunized animals exhibited moderate to high levels of tissue parasitism.

Markedly, in Mut-immunized mice, the extent of inflammation and accompanying tissue damage in heart and skeletal muscle was remarkably reduced or virtually absent after infection (FIG. 9, Panels C, F, I). In contrast, WT- or OCH1-immunized mice showed partial amelioration of their muscle and myocardial lesions (FIG. 9, Panels B, E, H). Although most control animals (60 to 90%) died, the few survivors showed extensive skeletal muscle inflammation and tissue necrosis, the hallmarks of Chagas' disease. Finally, as can be seen in Table II, no inflammatory lesions were recorded in non-infected mice, regardless of proteins administration.

Figure 10:
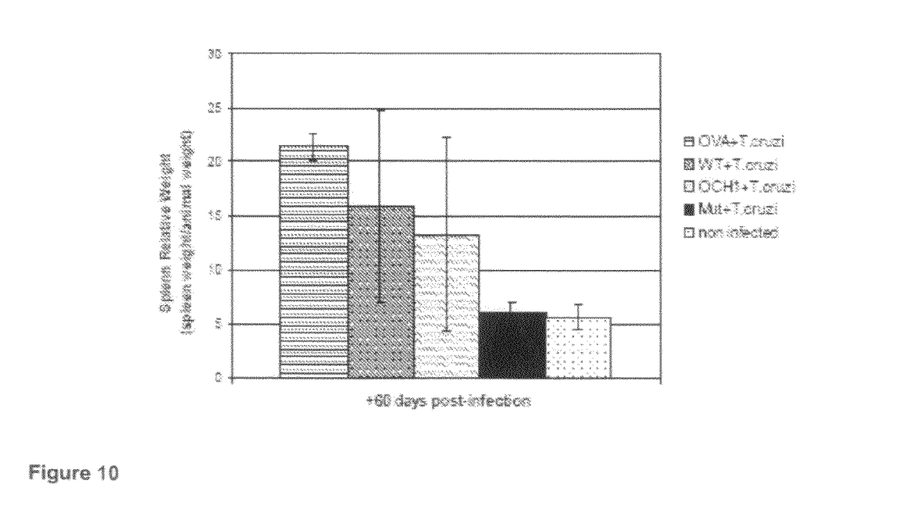
FIG. 10: Spleen weight changes in TSs-immunized and -challenged mice. Organ weight is presented as follows: (spleen weight (g)/total body weight (g)). Results represent the mean±SD after 60 days post-infection. Presented values correspond to one (OVA) of three non-immunized and infected mice and one of six non-immunized and non-infected control groups (similar results).

Splenomegaly and lymphadenopathy related to polyclonal B- and T-cell activation are typical features of *T. cruzi* infection (Olivieri et al., 2002). Also, the spleen is a common compromised organ in various animal models of Chagas' disease (Lima et al., 2001). For this reason, spleen weight from immunized and control mice on day 60 after *T. cruzi* challenge was analyzed (FIG. 10). Non-immunized and infected BALB/c mice displayed important splenomegaly. WT- and OCH1-treated groups developed moderate splenomegaly simultaneously with the presence of myocarditis or myositis. In these animals, the histological study revealed hyperplasia of the lymphoid follicles, with focal necrosis in germinal centers and red pulp in the absence of parasites. In contrast, no histological or spleen weight alterations were found in Mut-immunized mice, yielding data quite similar to the non-infected controls.

Infected, but untreated groups displayed liver focal infiltrates of amastigote-containing macrophages, either well preserved or in disintegration, with some hepatocyte necrosis in the focal areas.

Example 5

Figure 11:
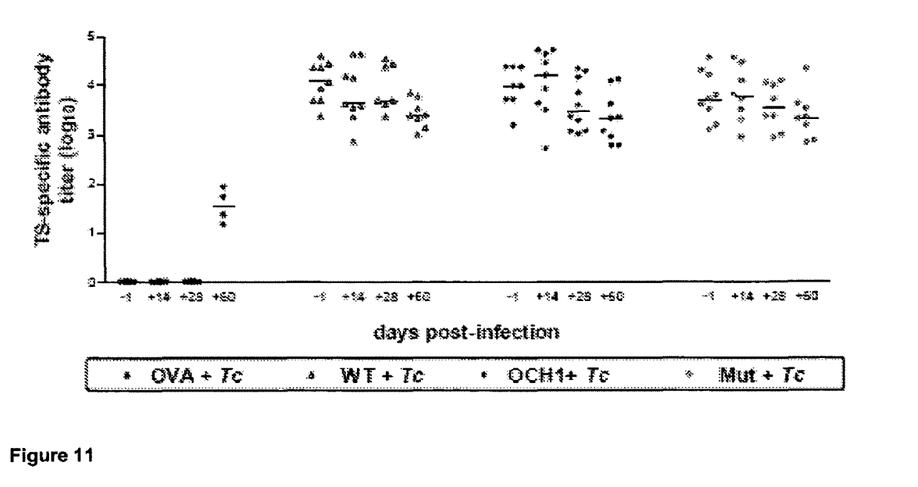
FIG. 11: Levels of anti-TS antibodies throughout *T. cruzi* infection. Individual values and median (horizontal bars) of each group. Infected WT, OCH1 or Mut TS groups had a trend to present higher specific TS antibodies levels than infected OVA mice. ($p<0.001$). Specific TS antibodies showed significant differences between OVA plus other control groups versus WT, OCH1 and Mut TS-immunized and non-infected mice, at all time points.
Figure 12:
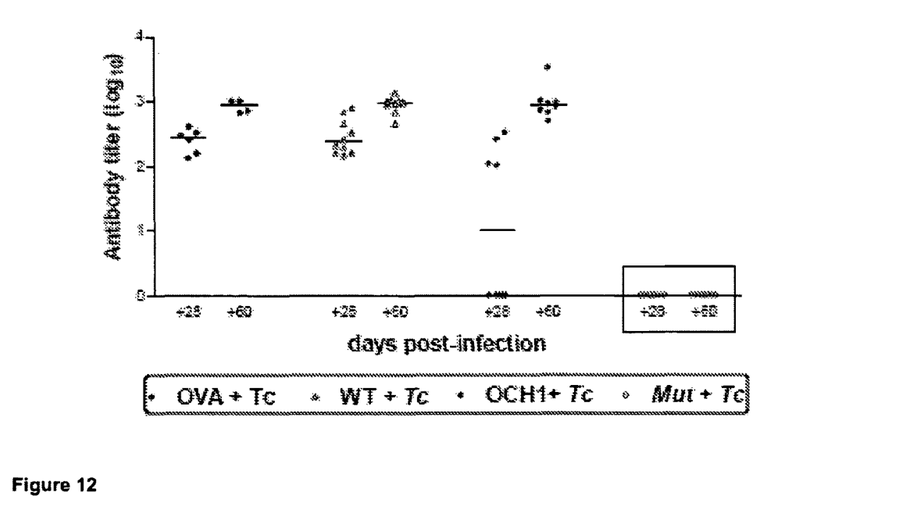
FIG. 12: Circulating levels of anti-SAPA antibodies during *T. cruzi* infection. Individual values and median (horizontal bars) of each group. After 28 days pi, OVA-, WT- and OCH1-infected groups had significantly higher amounts of specific anti-SAPA antibodies than infected Mut TS mice ($p<0.001$). In control mice, the results represent one (OVA) of three non-immunized and infected groups (similar results). At day −1 pi, specific anti-SAPA antibodies were undetectable in all groups. At day +14 pi, results were similar to day 28 pi.

Immunization with all Recombinant Proteins Stimulates Systemic Anti-TS Antibody Response but Infected Mut-Vaccinated Animals do not Induce Specific Anti-SAPA Humoral Response A kinetic study of specific anti-TS IgG response from immunized and control mice on day −1, +14, +28 and +60 before and after *T. cruzi* challenge was performed. High serum titers of anti-TSs IgGs were found in all immunized and/or infected groups at all time point evaluations (FIG. 11). Only at day +60 post-infection, low to moderate titers of anti-TS IgG were present in infected control animals (OVA+Tc, Adj+Tc and vehicle+Tc groups). As expected, there were no specific responses to all TSs in sera from non-immunized/non-infected control mice. Hence, the immunizations with TSs can stimulate a strong specific IgG antibody response, regardless of the recombinant protein administrated.

Because all recombinant TSs used in this study lacked the immunodominant SAPA repeats tail, immune responses directed against this repetitive domain resulted from parasite challenge, irrespective of inoculated TS protein. Mice were vaccinated as described in Materials and Methods and then assayed 14, 28 and 60 days after *T. cruzi* infection for the presence of specific anti-SAPA IgG antibody response (FIG. 11). Moderate (days 14 and 28) and high (day 60) levels of anti-SAPA-specific antibodies were detected in the sera of mice immunized with WT or OCH1 proteins and in non-immunized but infected mice (OVA+Tc group). Remarkably, recipients of the Mut protein did not reveal anti-SAPA antibodies (p<0.001), which is an indication of an efficient control of the infection. Finally, anti-SAPA-specific antibodies were not detectable in sera collected before the *T. cruzi* infection. The presence of circulating anti-SAPA antibodies was correlated with a worsened course of infection. As anti-SAPA antibodies are not protective, the absence of anti-SAPA antibodies is a clear advantage as this is avoiding the distraction of the immune system, and creating an effective immune response toward the important catalytic site of the enzyme. Indeed, mice immunized with Mut TS protein not only survived *T. cruzi* infection but also controlled the blood and tissue parasite burden while exhibiting a dramatic reduction in skeletal and heart muscle inflammation and necrosis during the late phase of the infection. These results indicate that effective immunological control of parasite load during the acute and chronic phases of infection, as obtained with the Mut TS vaccine, results in reduced tissue parasite load and associated decreases in disease intensity. It is clear from these results that the severity of tissue injury in *T. cruzi* infection is tightly linked to the relative success in limiting parasite levels and that such a successful limitation, as proved by the level of anti-SAPA antibodies, is only obtained by the Mut TS vaccine.

TABLE 1

| | Non-Infected | | | | Infected | | | |
|---|---|---|---|---|---|---|---|---|
| | WT | OCH1 | Mut | OVA | WT | OCH1 | Mut | OVA |
| Myositis | | | | | | | | |
| Mice with FM/total | 0/5 | 0/5 | 0/5 | 0/5 | 6/9 | 5/9 | 1/10 | 4/4 |
| Small Sized | | | | | 1 | 2 | 1 | |
| Medium Sized | | | | | 2 | 2 | | 1 |
| Large Sized | | | | | 3 | 1 | | 3 |
| Amastigotes nests | | | | | — | — | — | ++++ |
| Myocarditis | | | | | | | | |
| Mice with FM/total | 0/5 | 0/5 | 0/5 | 0/5 | 5/9 | 3/9 | 0/10 | 4/4 |
| Small Sized | | | | | 2 | 2 | | 1 |
| Medium Sized | | | | | 3 | 1 | | 3 |
| Large Sized | | | | | | | | |
| Amastigotes nests | | | | | — | — | — | ++++ |

REFERENCES

Bradford M. M. (1976). A rapid and sensitive method for the quantitation of microgram quantities of protein utilizing the principle of protein-dye binding. *Anal. Biochem.* 72:248-254.

Callewaert N., S. Geysens, F. Molemans, and R. Contreras (2001). Ultrasensitive profiling and sequencing of N-linked oligosaccharides using standard DNA-sequencing equipment. *Glycobiology* 11(4):275-281.

Ciavaglia M., T. U. de Carvalho, and W. de Souza (1993). Interaction of *Trypanosoma cruzi* with cells with altered glycosylation patterns. *Biochem. Biophys. Res. Commun.* 193:718-721.

Costa F., G. Francjin, V. L. Pereira-Chioccola, M. Ribeirao, S. Schenkman, and M. Rodrigues, M. M. (1998). Immunization with a plasmid containing the gene of trans-sialidase reduces *Trypanosoma cruzi* infection in mice. *Vaccine* 16:768-774.

El-Sayed N. M., P. J. Myler, D. C. Bartholomeu, D. Nilsson, G. Aggarwal, A. N. Tran, E. Ghedin, E. A. Worthey, A. L. Delcher, G. Blandin, S. J. Westenberger, E. Caler, G. C. Cerqueira, C. Branche, B. Haas, A. Anupama, E. Arner, L. Åslund, P. Attipoe, E. Bontempi, F. Bringaud, P. Burton, E. Cadag, D. A. Campbell, M. Carrington, J. Crabtree, H. Darban, J. F. da Silveira, P. de Jong, K. Edwards, P. T. Englund, G. Fazelina, T. Feldblyum, M. Ferella, A. C. Frasch, K. Gull, D. Horn, L. Hou, Y. Huang, E. Kindlund, M. Klingbeil, S. Kluge, H. Koo, D. Lacerda, M. J. Levin, H. Lorenzi, T. Louie, C. R. Machado, R. McCulloch, A. McKenna, Y. Mizuno, J. C. Mottram, S. Nelson, S. Ochaya, K. Osoegawa, G. Pai, M. Parsons, M. Pentony, U. Pettersson, M. Pop, J. L. Ramirez, J. Rinta, L. Robertson, S. L. Salzberg, D. O. Sanchez, A. Seyler, R. Sharma, J. Shetty, A. J. Simpson, E. Sisk, M. T. Tammi, R. Tarleton, S. Teixeira, S. Van Aken, C. Vogt, P. N. Ward, B. Wickstead, J. Wortman, O. White, C. M. Fraser, K. D. Stuart, and B. Andersson (2005). The genome sequence of *Trypanosoma cruzi*, etiologic agent of Chagas disease. *Science* 309(5733):409-415.

Katae M., Y. Miyahara, K. Takeda, H. Matsuda, H. Yagita, K. Okumura, T. Takeuchi, T. Kamiyama, A. Ohwada, Y. Fukuchi, and T. Aoki (2002). Coadministration of an interleukin-12 gene and a Trypanosome *cruzi* gene improves vaccine efficacy. *Infect. Immun.* 70:4833-4840.

Laroy W. and R. Contreras (2000). Cloning of *Trypanosoma cruzi* trans-sialidase and expression in *Pichia pastoris*. *Protein expression and purification* 20:389-393.

Lima E. S., Z. A. Andrade, and S. G. Andrade (2001). TNF-alpha is expressed at sites of parasite and tissue destruction in the spleen of mice acutely infected with *Trypanosoma cruzi*. *Int. J. Exp. Pathol.* 82:327-336.

Ming M., M. Chuenkova, E. Ortega-Barria, and M. E. A. Pereira (1993). Mediation of *Trypanosoma cruzi* invasion by sialic acid on the host cell and trans-sialidase on the trypanosome. *Mol. Biochem. Parasitol.* 59:243-252.

Olivieri B. P., V. Cotta-De-Almeida, and T. Araujo-Jorge (2002). Benznidazole treatment following acute *Trypanosoma cruzi* infection triggers CD8+ T-cell expansion and promotes resistance to reinfection. *Antimicrob. Agents Chemother.* 46:3790-3796.

Pereira-chioccola V. P., F. Costa, M. Ribeirao, I. S. Soares, F. Arena, S. Schenkman, and M. M. Rodrigues (1999). Comparison of antibody and protective immune responses against *Trypanosoma cruzi* infection elicited by immunization with a parasite antigen delivered as naked DNA or recombinant protein. *Parasite Immunology* 21:103-110.

Roggero E., A. Perez, M. Tamae-kakazu, I. Piazzon, I. Nepomnaschy, and J. Wietzerbin (2002). Differential susceptibility to acute *Trypanosoma cruzi* infection in BALB/c and C57BL/6 mice is not associated with distinct parasite load but cytokine abnormalities. *Clin. Exp. Immunol.* 128:421-428.

Ruiz R., V. L. Rigoni, J. Gonzalez, N. Yoshida (1993). The 35/50 kDa surface antigen of *Trypanosoma cruzi* metacyclic trypomastigotes, an adhesion molecule involved in host cell invasion. *Parasitol. Immunol.* 15:121-125.

Schenkman R. P. S., F. Vandekerckhove, and S. Schenkman (1993). Mammalian cell sialic acid enhances *Trypanosoma cruzi* invasion. *Infect. Immun.* 61:898-902.

Schenkman S., M. Jiang, G. W. Hart, and V. Nussenzweig (1991). A novel cell surface trans-sialidase of *Trypanosoma cruzi* generates a stage-specific epitope required for invasion of mammalian cells. *Cell* 65:1117-1125.

Vasconcelos J. R., M. I. Hiyane, C. R. Marhino, C. Claser, A. M. Machado, R. T. Gazzinelli, O. Bruna-Romero, J. M. Alvarez, S. B. Boscardin, and M. M. Rodrigues (2004). Protective immunity against Trypanosome *cruzi* infection in a highly susceptible mouse strain after vaccination with genes encoding the amastigote surface protein-2 and trans-sialidase. *Hum. Gene Ther.* 15:878-886.

Vervecken W., V. Kaigorodov, N. Callewaert, S. Geysens, K. De Vusser, and R. Contreras (2004). In vivo synthesis of mammalian-like, hybrid-type N-glycans in *Pichia pastoris*. *Appl. Environ. Microbiol.* 70(5):2639-2646.

Woronowicz A., K. De Vusser, W. Laroy, R. Contreras, S. O. Meakin, G. M. Ross, and M. R. Szewczuk (2004). Trypanosome trans-sialidase targets TrkA tyrosine kinase receptor and induces receptor internalization and activation. *Glycobiology* 14(11):987-998.

Yoshida N., R. N. Mortara, M. F. Araguth, J. D. Gonzalez, and M. Russo (1989). Metacyclic neutralizing effect of monoclonal antibody 10D8 directed to the 35- and 50-kilodalton surface glycoconjugates of *Trypanosoma cruzi*. *Mol. Biochem. Parasitol.* 39:39-46.

---

The invention claimed is:

1. A method of treating Chagas disease in a subject, the method comprising administering an immunogenic composition to the subject, the immunogenic composition comprising:
    an amount of an enzymatically inactive *Trypanosoma* trans-sialidase mutant protein, wherein the enzymatically inactive *Trypanosoma* trans-sialidase mutant protein is a recombinant mutant trans-sialidase lacking the immunodominant shed acute-phase antigen repeats tail, and wherein the recombinant mutant trans-sialidase comprises SEQ ID NO:1, sufficient to induce an immune response against *Trypanosoma cruzi* in the subject.

2. The method according to claim 1, wherein the recombinant mutant trans-sialidase has a modified glycosylation pattern compared to wild-type trans-sialidase.

3. A method of inducing an immune response in a subject against *Trypanosoma cruzi*, the method comprising administering to the subject a composition comprising:
    an amount of an enzymatically inactive *Trypanosoma* trans-sialidase mutant protein, wherein the enzymatically inactive *Trypanosoma* trans-sialidase mutant protein is a recombinant mutant trans-sialidase lacks the immunodominant shed acute-phase antigen repeats tail, and wherein the recombinant mutant trans-sialidase comprises SEQ ID NO:1,
    so as to induce the immune response in the subject.

4. The method according to claim 3, wherein the recombinant mutant trans-sialidase has a modified glycosylation pattern compared to wild-type trans-sialidase.

5. The method of claim 3, wherein the composition consists of enzymatically inactive *Trypanosoma* trans-sialidase mutant protein as active ingredient thereof.

\* \* \* \* \*

SEQUENCE LISTING

```
<160> NUMBER OF SEQ ID NOS: 1

<210> SEQ ID NO 1
<211> LENGTH: 643
<212> TYPE: PRT
<213> ORGANISM: Artificial
<220> FEATURE:
<223> OTHER INFORMATION: Mutant trans-sialidase

<400> SEQUENCE: 1

Met Val Leu Ala Pro Gly Ser Ser Arg Val Glu Leu Phe Lys Arg Lys
1               5                   10                  15

Asn Ser Thr Val Pro Phe Glu Asp Lys Ala Gly Lys Val Thr Glu Arg
            20                  25                  30
```

```
Val Val His Ser Phe Arg Leu Pro Ala Leu Val Asn Val Asp Gly Val
         35                  40                  45

Met Val Ala Ile Ala Asp Ala Arg Tyr Asp Thr Ser Asn Asp Asn Ser
 50                  55                  60

Leu Ile Asp Thr Val Ala Lys Tyr Ser Val Asp Asp Gly Glu Thr Trp
 65                  70                  75                  80

Glu Thr Gln Ile Ala Ile Lys Asn Ser Arg Val Ser Ser Val Ser Arg
                 85                  90                  95

Val Val Glu Pro Thr Val Ile Val Lys Gly Asn Lys Leu Tyr Val Leu
            100                 105                 110

Val Gly Ser Tyr Tyr Ser Ser Arg Ser Tyr Trp Ser Ser His Gly Asp
            115                 120                 125

Ala Arg Asp Trp Asp Ile Leu Leu Ala Val Gly Glu Val Thr Lys Ser
            130                 135                 140

Ile Ala Gly Gly Lys Ile Thr Ala Ser Ile Lys Trp Gly Ser Pro Val
145                 150                 155                 160

Ser Leu Lys Lys Phe Phe Pro Ala Glu Met Glu Gly Met His Thr Asn
                165                 170                 175

Gln Phe Leu Gly Gly Ala Gly Val Ala Ile Val Ala Ser Asn Gly Asn
            180                 185                 190

Leu Val Tyr Pro Val Gln Val Thr Asn Lys Arg Lys Gln Val Phe Ser
            195                 200                 205

Lys Ile Phe Tyr Ser Glu Asp Asp Gly Lys Thr Trp Lys Phe Gly Lys
            210                 215                 220

Gly Arg Ser Asp Phe Gly Cys Ser Glu Pro Val Ala Leu Glu Trp Glu
225                 230                 235                 240

Gly Lys Leu Ile Ile Asn Thr Arg Val Asp Trp Lys Arg Arg Leu Val
                245                 250                 255

Tyr Glu Ser Ser Asp Met Gly Asn Thr Trp Val Glu Ala Val Gly Thr
            260                 265                 270

Leu Ser Arg Val Trp Gly Pro Ser Pro Lys Ser Asp Gln Pro Gly Ser
            275                 280                 285

Gln Ser Ser Phe Thr Ala Val Thr Ile Glu Gly Met Arg Val Met Leu
            290                 295                 300

Phe Thr His Pro Leu Asn Phe Lys Gly Arg Trp Leu Arg Asp Arg Leu
305                 310                 315                 320

Asn Leu Trp Leu Thr Asp Asn Gln Arg Ile Tyr Asn Val Gly Gln Val
                325                 330                 335

Ser Ile Gly Asp Glu Asn Ser Ala Tyr Ser Ser Val Leu Tyr Lys Asp
            340                 345                 350

Asp Lys Leu Tyr Cys Leu His Glu Ile Asn Thr Asp Gly Val Tyr Ser
            355                 360                 365

Leu Val Phe Ala Arg Leu Val Gly Glu Leu Arg Ile Ile Lys Ser Val
            370                 375                 380

Leu Arg Ser Trp Lys Asn Trp Asp Ser His Leu Ser Ser Ile Cys Thr
385                 390                 395                 400

Pro Ala Asp Pro Ala Ala Ser Ser Glu Ser Gly Cys Gly Pro Ala
                405                 410                 415

Val Thr Thr Val Gly Leu Val Gly Phe Leu Ser Gly Asn Ala Ser Gln
            420                 425                 430

Asn Val Trp Glu Asp Ala Tyr Arg Cys Val Asn Ala Ser Thr Ala Asn
            435                 440                 445
```

-continued

```
Ala Glu Arg Val Arg Asn Gly Leu Lys Phe Ala Gly Val Gly Gly Gly
    450                 455                 460

Ala Leu Trp Pro Val Ser Gln Gln Gly Gln Asn Gln Arg Tyr Arg Phe
465             470                 475                 480

Ala Asn His Ala Phe Thr Leu Val Ala Ser Val Thr Ile His Glu Ala
            485                 490                 495

Pro Arg Ala Ala Ser Pro Leu Leu Gly Ala Ser Leu Asp Ser Ser Gly
            500                 505                 510

Gly Lys Lys Leu Leu Gly Leu Ser Tyr Asp Glu Lys His Gln Trp Gln
        515                 520                 525

Pro Ile Tyr Gly Ser Thr Pro Val Thr Pro Thr Gly Ser Trp Glu Thr
    530                 535                 540

Gly Lys Arg Tyr His Val Val Leu Thr Val Ala Asn Lys Ile Gly Ser
545             550                 555                 560

Val Tyr Ile Asp Gly Glu Leu Leu Glu Gly Ser Gly Gln Thr Val Val
            565                 570                 575

Pro Asp Gly Arg Thr Pro Asp Ile Ser His Phe Tyr Val Gly Gly Tyr
            580                 585                 590

Gly Arg Ser Asp Met Pro Thr Ile Ser His Val Thr Val Asn Asn Val
        595                 600                 605

Leu Leu Tyr Asn Arg Gln Leu Asn Thr Glu Glu Ile Arg Thr Leu Phe
        610                 615                 620

Leu Ser Gln Asp Leu Ile Gly Thr Glu Ala His Met Asp Ser Ser Ser
625             630                 635                 640

Asp Thr Lys
```